United States Patent [19]
Filhol

[11] Patent Number: 6,062,859
[45] Date of Patent: May 16, 2000

[54] DENTAL TOOL

[76] Inventor: Stuart Julian Filhol, Castlefreke, County Cork, Ireland, United Kingdom

[21] Appl. No.: 09/274,898

[22] Filed: Mar. 23, 1999

Related U.S. Application Data

[63] Continuation-in-part of application No. 08/737,962, filed as application No. PCT/GB95/01229, May 30, 1995, abandoned.

[30] Foreign Application Priority Data

May 31, 1994 [GB] United Kingdom ............... 9410831

[51] Int. Cl.⁷ ........................................... A61C 3/00
[52] U.S. Cl. ...................... 433/165; 408/231; 408/239 A
[58] Field of Search .................................. 433/134, 135, 433/142, 165, 166; 279/143, 906; 408/231, 238, 239 A, 239 R

[56] References Cited

U.S. PATENT DOCUMENTS

| | | | |
|---|---|---|---|
| 4,006,787 | 2/1977 | Rumpp et al. | 279/906 |
| 4,035,100 | 7/1977 | Kruger et al. | 408/226 |
| 4,413,937 | 11/1983 | Gutsche | 408/239 |
| 4,478,578 | 10/1984 | Leonard | 433/165 |
| 5,211,560 | 5/1993 | Lowder et al. | 433/166 |
| 5,342,200 | 8/1994 | Chalifoux | 433/165 |

OTHER PUBLICATIONS

Einfuhrung in Die Din–Normen, B.G. Teubner, Stuttgart Din 1481 (Nov. 1959) and DIN 7346 (Jul. 1960) pp. 566–567.

*Primary Examiner*—Ralph A. Lewis
*Attorney, Agent, or Firm*—Ostrolenk, Faber, Gerb & Soffen, LLP

[57] ABSTRACT

A dental tool holder (2) and/or tool (23) having a tip (22) is made by non-cutting deformation of metal blank (1, 16) and optionally removal of material to provide the dental tool with a pointed tip (22). The blank may have a first part (3, 11) which can define a groove (4), a second part (5, 12) which can be folded to form a shaft (6) and optionally an integral tool forming portion (13).

7 Claims, 5 Drawing Sheets

6,062,859

DENTAL TOOL

RELATED APPLICATION

This application is a continuation-in-part of U.S. Ser. No. 08/737,962 filed Dec. 2, 1996 now abandoned and derived from PCT/GB95/01229 (WO95/32680) of May 30, 1995, all filed by Stuart J. Filhol.

BACKGROUND OF THE INVENTION

The present invention relates to dental tools and in particular dental tools capable of releasable attachment to an automatic tool driver.

A conventional dental tool assembly is disposable and comprises a dental tool such as a pin, drill, burr or reamer which is fixed to, or forms an integral part of, a tool holder. The tool holder may be provided with a latching groove or other suitable means for engagement with the driving mechanism of a dental tool driver designed to rotate the entire assembly at variable speed.

The dental tool driver has a size such that it can be held and operated manually, whereas the dental tool holder is usually very small, only a few centimetres long. The dental tool driver conventionally has a combined latching and driving mechanism into which the end of the dental tool holder is fitted.

The combined latching and driving mechanism includes a substantially flat (or otherwise appropriately shaped) driving surface which engages with a correspondingly shaped (usually flat) mating, surface at one side of the end of the driver. The driving surface rotates around the axis of the holder and thereby rotates the holder and the dental tool fixed in it. The latching and driving mechanism also has a latch which engages within a groove in the holder transverse to the axis of the holder whereby the holder is held in position so that the driving surface can drive the driven surface without any risk of the holder falling out of the latching and driving mechanism. This arrangement is conventional and is widely used in dental apparatus.

Usually, the dental tool is formed separately from the holder using conventional metal cutting techniques and is subsequently attached to the tool holder. Suitable materials for manufacturing dental tools include titanium, gold, and special graded stainless tool steels.

The tool holder may be machined from a suitable source of material and is provided with a longitudinal bore at the end distant from the latching groove and into which an extended shank of the dental tool may be inserted. The dental tool is usually fixed within the tool holder either by punching the tool holder to cause a permanent interlocking distortion or by applying a force along the longitudinal axis of the dental tool positioned within the longitudinal bore to permanently concertina the tool shank thereby locking the two together. Alternatively, a plastic tool holder may be moulded around the pre-formed dental tool.

In another production technique the entire tool assembly is machined from a single length of metal material to form the dental tool as an integral part of the tool holder.

A typical production line using the above techniques produces around five tool assemblies per minute. This relatively slow production process means that the unit price for each tool assembly is high.

OBJECTS OF THE INVENTION

It would be desirable to devise a simpler and more economical way of constructing a dental tool holder.

SUMMARY OF THE INVENTION

According to the invention, a dental tool holder is made by non-cutting deformation of a metal blank and, optionally, removal of material to provide the dental tool with a pointed tip.

According to a first aspect of the present invention, a dental tool holder is formed of a folded blank of sheet metal. The holder can be very cheap to manufacture and so can be treated as a disposable holder.

The present invention also includes a sheet metal blank which may be folded using metal forming techniques to produce a dental tool holder.

In particular, the invention provides a dental tool holder which comprises a longitudinally extending substantially tubular shaft having a tool end and a latching end distant from the tool end, tool securing means at the tool end for mounting the tool, or at which the tool is mounted, for rotation with the shaft, a latching groove at the latching end and adapted to latchably engage with a dental tool driver whereby the shaft extends from the driver to the tool and the shaft and the tool are co-rotatable by the driver, and wherein the holder has been formed by folding a sheet metal blank having a shaft portion and a latching portion, wherein the shaft portion of the blank has an axial length which defines the distance between the tool end and the latching end, and a width which is sufficient to substantially provide the periphery of the substantially tubular shaft, and the shaft portion has been folded substantially parallel to the length of the holder to provide the substantially tubular shaft, the latching portion of the blank is integral with the shaft portion and comprises a first transverse flange integral with the shaft portion and a second transverse flange connected to the first flange by a web which is narrower than each of the flanges, and the first flange has been folded substantially parallel to the length of the holder to define a substantially flat drive surface for driving engagement with a drive member in the dental tool driver, and the second flange is folded substantially parallel to the length of the holder to provide a substantially tubular abutment separated from but connected to the folded first flange by the web, the web and the folded first and second flanges thereby defining the latching groove, and in which the tool end of the shaft is adapted to receive a preformed dental tool, or a dental tool is integral with the tool end of the shaft and extends away from the tool end.

DESCRIPTION OF THE PREFERRED EMBODIMENTS

Metal forming techniques are generally faster than metal cutting techniques so that the production rate is significantly increased to around one hundred units per minute. Furthermore, forming the tool holder from a sheet metal blank generally uses significantly less material and is therefore, less expensive.

Preferably, the sheet metal blank has a thickness around 0.1 mm and 0.3 mm, usually between 0.15 mm and 0.20 mm.

Preferably, the sheet metal blank comprises a latching, or first, portion which when folded forms a latching groove for engagement with a tool driver and a shaft, or second, portion which when folded defines a longitudinally extending substantially tubular shaft and optionally an integral tool-forming portion.

In one embodiment, preferably the shaft or second portion is folded to define a substantially tubular shaft which is adapted to receive a pre-formed dental tool within the shaft. The dental tool may be secured in place by securing means at the end of the tubular shaft distant from the latching groove, thereby holding the tool in the holder by interlocking engagement to provide an assembly of the holder and the tool. For instance the end of the shaft may be deformed into interlocking engagement with the tool. An adhesive may also be used either alone or in combination with the securing means. These may be a deformed part of the shaft. Preferably, some or all of the tubular shaft which as been folded from the blank has the form a resiliently flexible clamp which resists removal of a dental tool held in the shaft and resists relative movement between the dental tool and the tool holder.

In a second embodiment, the second portion includes an integral tool-forming portion which may be formed into an integral dental tool. The dental tool-forming portion of the blank may be formed into a tool such as a dental pin, drill or reamer by working the material of at least a lower part of the tool-forming portion material into the required shape and configuration using conventional techniques. Alternatively a drill may be formed by compressing a length of metal material between opposing surfaces and subsequently removing material at one end to obtain a pointed tip.

Thus a disposable dental drill assembly may be produced by folding the sheet metal blank to form the tool holder and subsequently compressing the material of the tool-forming portion and removing material at one end to form an integral dental drill with a pointed tip.

The metal material may be compressed between opposing surfaces to shape the transverse cross section of the drill. Preferably, the finished drill has a parallelogram-shaped transverse cross section. The drill may be provided with a degree of twist although preferably the drill is substantially flat.

Examples of the present invention will now be described with reference to the accompanying drawings, in which.

Figure 1:
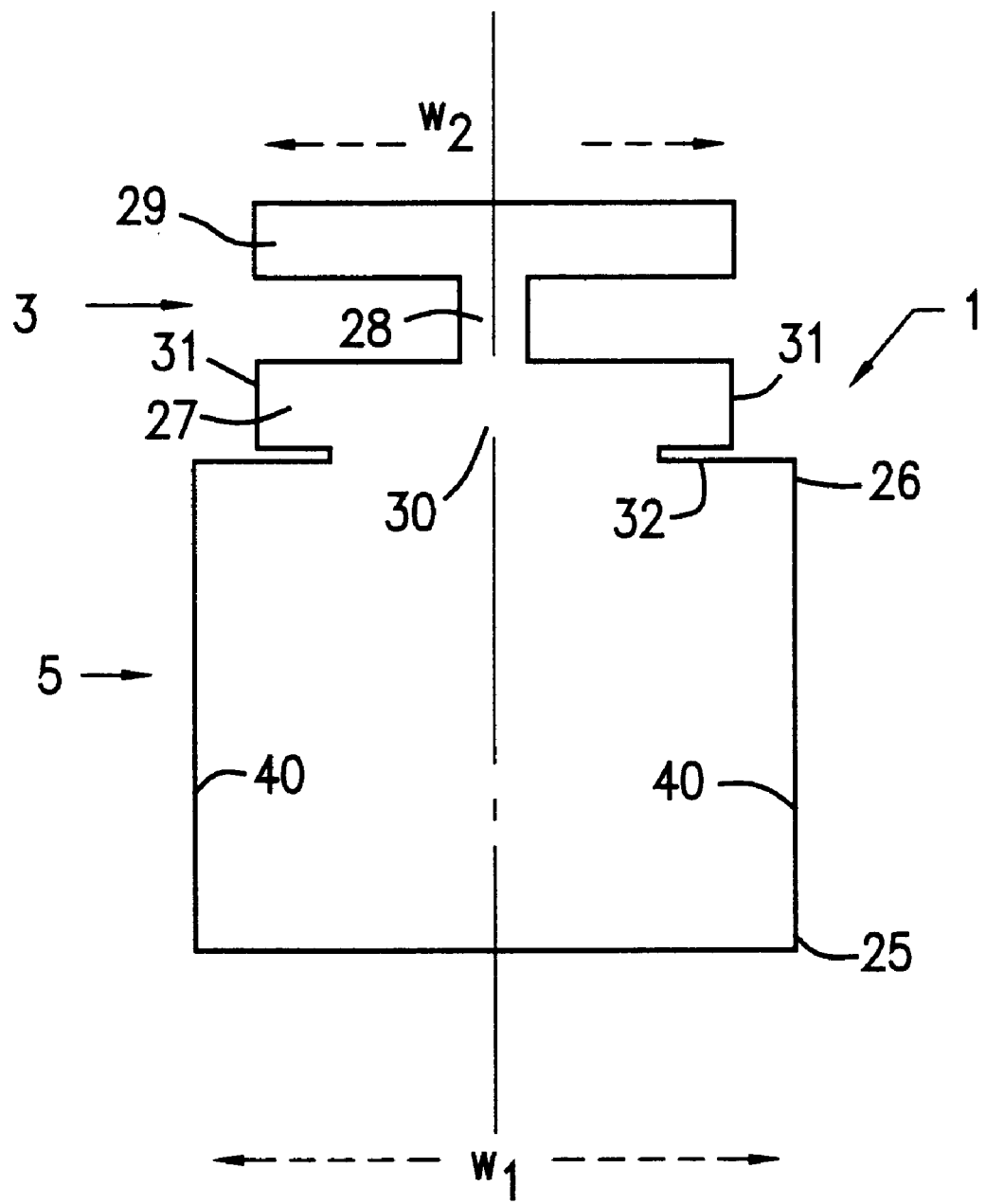
FIG. 1 shows a plan view of one example of a sheet metal blank in accordance with the first aspect of the present invention.
Figure 3:
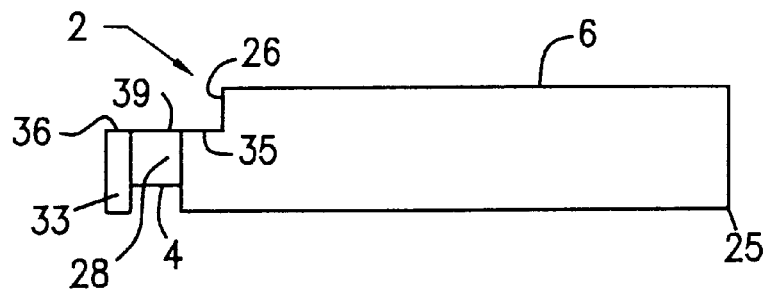
FIG. 3 shows a side view of the folded blank of FIG. 1.

FIG. 1 shows a sheet metal blank 1 which is approximately 0.15 to 0.20 mm thick which is folded to form a tool holder 2 shown in side view in FIG. 3. The blank 1 comprises a latch or first portion 3 which when folded forms a latching groove 4 for engagement with the driving mechanism of a conventional automatic tool driver designed to rotate the entire assembly at variable speeds (not shown). The blank 1 also comprises a shaft or second portion 5 which when folded defines a longitudinally extending tubular shaft 6. This may be substantially cylindrical or may have any other suitable tubular shape. Typically, the sheet metal blank 1 is manufactured from high speed steel, stainless steel or brass.

In more detail, the shaft portion 5 extends from a tool end 25 to a latching end 26 where it is integral with a first transverse flange 27, a narrow web 28 and a second transverse flange 29. The flanges 27 and 29 and the web 28 constitute the latching portion. Preferably each of the flanges is slightly narrower than the width of the shaft portion 3. The first flange is integral with the shaft portion over its central region 30 but is separated from the shaft portion at its outermost edges 31 by inwardly extending slits 32.

Figure 2:
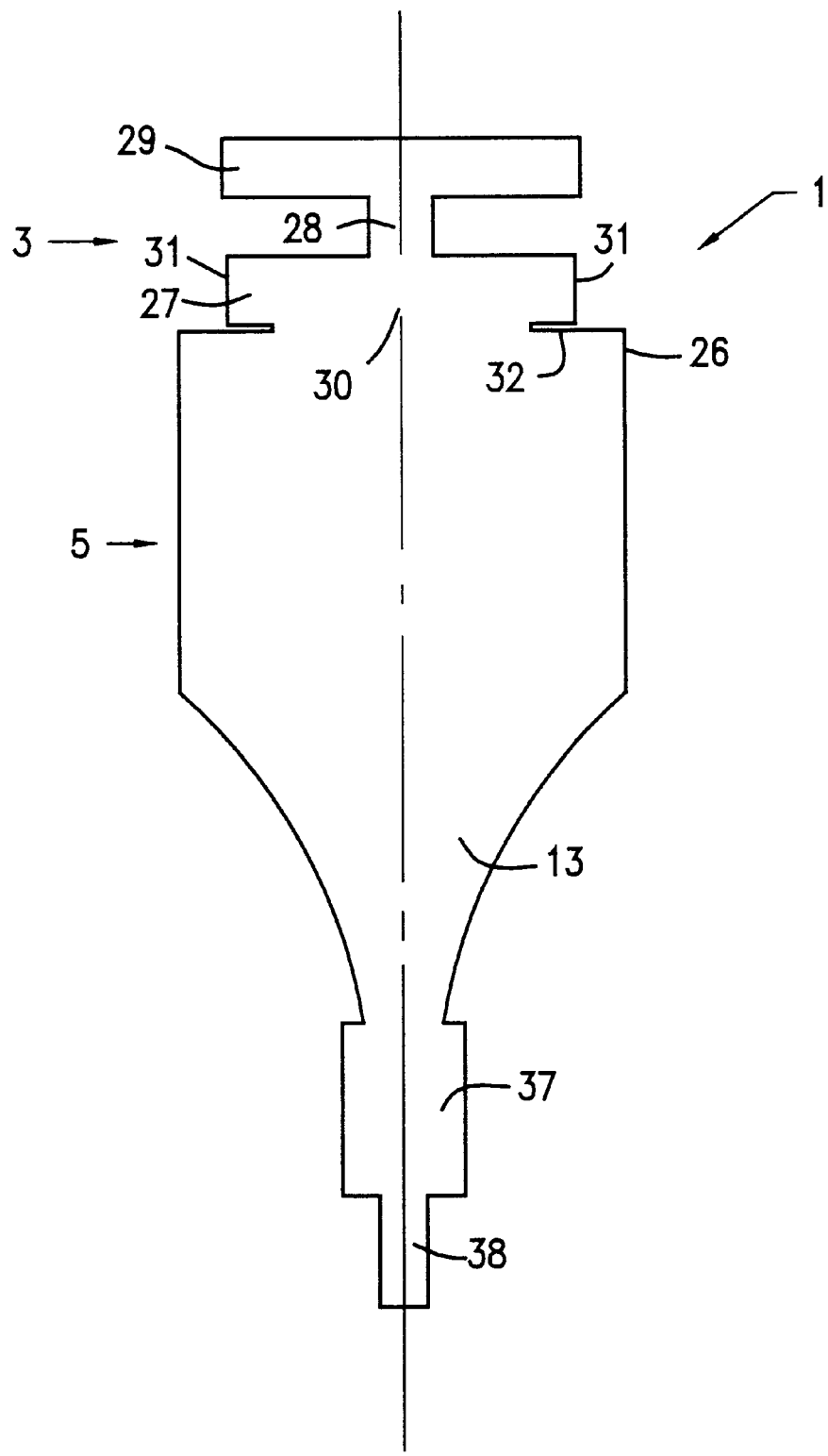
FIG. 2 shows a plan view of another example of a sheet metal blank in accordance with the present invention.

FIG. 2 shows another sheet metal blank 1 comprising a shaft portion 5 and a latching portion 3. It will be seen that it is of similar instruction to the blank in FIG. 1 except that the shaft portion 5 includes a tapered section 13 which may lead into an integral dental tool-forming extension 38. A dental tool 14 (see FIG. 4) may be formed from the extension 38 by working the material of that lower part 38 of the blank to the required shape and configuration using conventional techniques. The blank may have a wider section 37 at the end of the tapered part 13 either to provide extra material to facilitate forming the tool, or to provide a stop to facilitate manufacture or use. Further, in another embodiment the tool-forming extension 38 may be omitted and the wider section 37 may be folded to provide a channel for receiving a dental tool.

Figure 4:
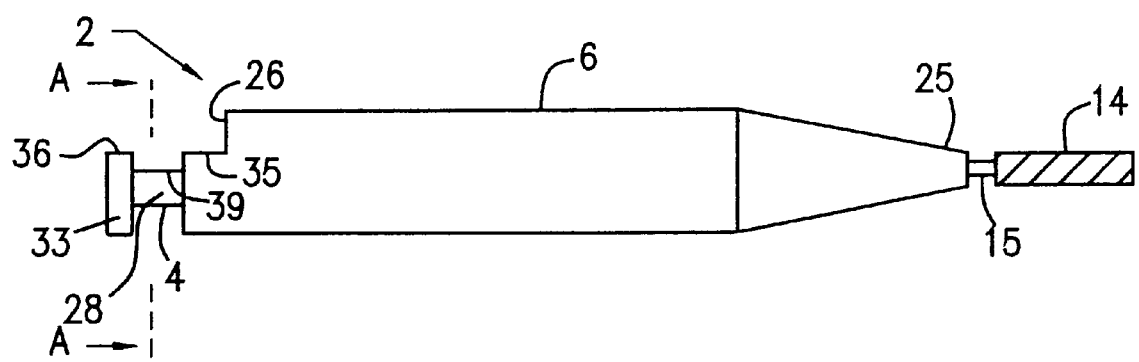
FIG. 4 shows a side view of the folded blank of FIG. 2.

FIG. 4 shows a side view of the folded blank of FIG. 2 in which the tool-forming portion 13 has been worked to provide a dental pin 14. A low shear portion 15 is provided to allow the dental pin 14 to be separated from the tool holder.

As shown in FIGS. 3 and 4, the blank is folded to provide a dental tool holder comprising a substantially tubular shaft 6 having a tool end 25 and a latching end 26. At the latching end there is tubular abutment 33, a latching groove 4 and a substantially flat drive surface 35. Conveniently this drive surface 35 is substantially co-planar with a corresponding drive surface 36 on the tubular abutment. As a result of providing drive surfaces 35 and 36, the drive forces are applied (at least in part) direct to the tubular shaft and so they are not applied to the shaft solely through the web. The precise configuration and position of the upper surface 39 formed by the web 28 and which extends between the drive surfaces 35 is less important. It may be substantially co-planar as shown in FIG. 3 or may be recessed downwardly as shown in FIG. 4.

Figure 5:
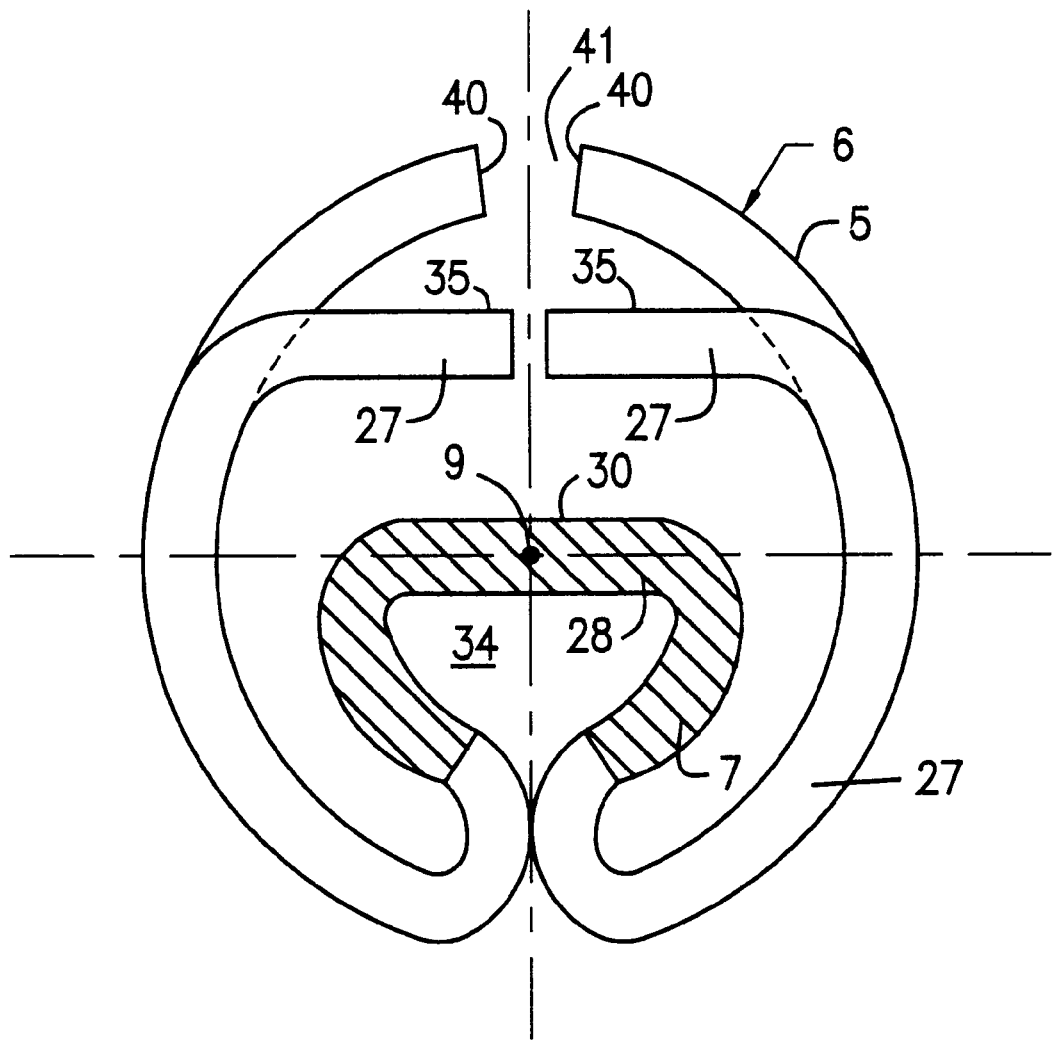
FIG. 5 shows a cross section taken through the line A—A of FIG. 4.

FIG. 5 is a cross section taken through the latching groove 4, and thus through the web 28, for instance on the line A—A as shown in FIG. 4.

The shaft portion 5 is folded substantially parallel to the length of the holder so as to provide a substantially tubular body 6. The width of the shaft portion 5 must be sufficiently great to allow the formation of a substantially tubular body but it does not have to be sufficiently great for the opposing edges 40 of the shaft portion to abut to one another. Instead the tubular body can be open, as shown at 41. The first transverse flange 27 is folded inwardly so as to define the substantially flat surface 35 which can be engaged by the driving mechanism of the tool driver, so as to cause rotation of the tool holder. It is generally convenient for the flange 27 to be slightly narrower than the width of the shaft portion 5 (i.e. W2 is less than W1) so as to facilitate folding the flange 27 to provide a flat surface 35 radially inwards of the periphery of the tubular shaft. This means that the end 26 of the shaft provides a stop which prevents the shaft being pushed too far into the driving and latching mechanism of the driver.

The second flange 29 is generally folded in the same configuration as the first flange 27 so as to provide a tubular abutment 33 to prevent the holder sliding out of the latching and driving mechanism of the driver, when the latch is engaged with the latching groove 4.

The web 28 interconnects the folded first and second flanges and can be in any configuration that allows for this and which does not interfere with the operation of the latching mechanism. Indeed, it is not essential that it should be folded and it can remain as a flat narrow sheet.

A tool can be fitted in the tool end 25 in any convenient manner. For instance a tool can be mounted in a plug which fits within the cylindrical or other shaped tubular end 25, for instance with deformation of the tube and/or with the assistance of adhesive. Naturally the tool must be mounted so that the longitudinal axis of the tool is aligned with the rotation axis 9 of the tool holder.

It is often convenient for the blank to be folded along its entire length and in the embodiment shown in FIG. 5 the central part 30 of the blank which is aligned with the tool-forming part 38 (and the tool 14) is folded along the length of the holder so as to lie along the rotational axis 9 and defines a channel 34. Although the channel 34 can have any desired shape in the embodiments such as FIG. 4 (having an integral tool), preferably it is shaped so that it can receive and hold the shank of a preformed tool, at its tool end. This in the embodiment of FIG. 3 the channel 34 may be substantially cylindrical, and preferably it is centred on the rotational axis 9. The channel 34 has a smaller diameter than the shaft and is located within the shaft, usually coaxial with the shaft. The web 28 can therefore be folded into the configuration of a flexible resilient clip 7 and the dental tool can be received in the channel 34 defined by this spring clip and secured in it.

The dental tool may be secured in place by punching the tool holder to cause a permanent interlocking distortion (not shown). Alternatively, or even additionally, adhesive may be used. The dental tool (not shown) itself is cranked, if necessary, to ensure that the longitudinal axis of the tool is aligned with the rotational axis 9 of the tool holder 2.

In the embodiment shown in FIG. 5 the spring clip and the channel 34 therefore extend along substantially the entire length of the tubular shaft 6 but if desired they can be formed only at the drilling end, for instance as a result of providing slits near the end 25 extending inwardly from the outer edges 32 sufficient to allow the end 25 of the shaft portion to be deformed to provide the spring clip or other channel arrangement 34 only at the tool end.

Figure 6:
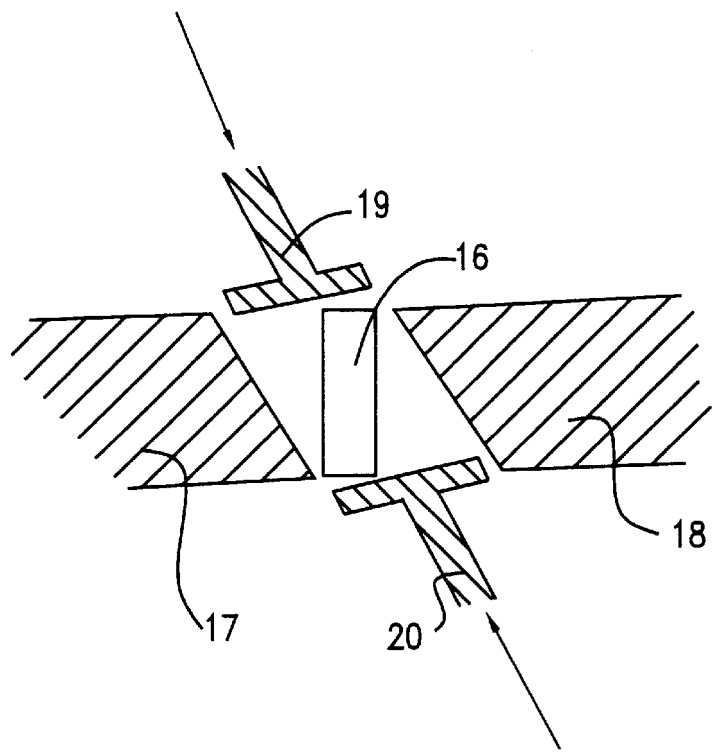
FIG. 6 shows a method of forming a drill in accordance with the second aspect of the present invention.
Figure 7A:
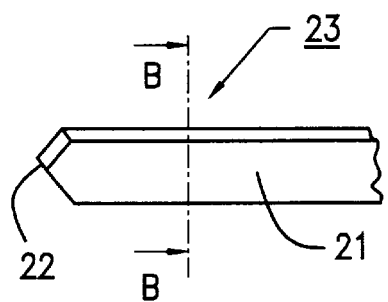
FIG. 7A shows a drill made in accordance with the second aspect of the present invention; and, FIG. 7B shows a cross section of the drill shown in FIG. 7A taken along the line B—B.
Figure 7B:
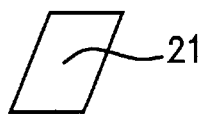

FIGS. 6 and 7 illustrate a method of forming a drill 23 in accordance with the second aspect of the present invention. A length of material 16 (shown here in cross section) is positioned between two opposing blocks 17 and 18 and is subsequently compressed between two opposing pistons 19 and 20 to obtain a body 21 having a parallelogram shaped transverse cross section. Cutting material from one end to provide a pointed tip 22 produces a drill 23. Such a drill lends itself well to the field of dentistry in which there is a need for a cheap disposable drill. The drill 23 may be provided with an integral shank portion (not shown) for fitting to the tool holder 2 shown in FIG. 3. Alternatively, the end of the tool-forming portion 13 of the blank 10 shown in FIG. 2 may be compressed and subsequently cut to provide a pointed drill.

In this example, the opposing blocks 17 and 18 are shaped so that the body 21 has a parallelogram-shaped transverse cross section and the finished drill 23 is substantially flat. However, the opposing blocks may be of any suitable shape so as to shape the drill correspondingly. The finished drill may be provided with a degree of twist.

I claim:

1. A holder for a dental tool selected from the group consisting of a dental pin, dental drill, dental burr and dental reamer wherein the holder comprises a longitudinally extending substantially tubular shaft having a tool end and a latching end distant from the tool end, tool securing means at the tool end for mounting the tool, or at which the tool is mounted, for rotation with the shaft, a latching groove at the latching end and adapted to latchably engage with a dental tool driver whereby the shaft extends from the driver to the tool and the shaft and the tool are co-rotatable by the driver, and wherein the holder has been formed by folding a sheet metal blank having a shaft portion and a latching portion, wherein the shaft portion of the blank has an axial length which defines the distance between the tool end and the latching end and a width which is sufficient to substantially provide the periphery of the substantially tubular shaft and the shaft portion has been folded substantially parallel to the length of the holder to provide the substantially tubular shaft, the latching portion of the blank is integral with the shaft portion and comprises a first transverse flange integral with the shaft portion and a second transverse flange connected to the first flange by a web which is narrower than each of the flanges, and the first flange has been folded substantially parallel to the length of the holder to define a drive surface for driving engagement with a drive mating member of the dental tool driver, and the second flange has been folded substantially parallel to the length of the holder to provide a substantially tubular abutment separated from but connected to the folded first flange by the web whereby the web and the folded first and second flanges define the latching groove and in which either the tool end of the shaft is adapted to receive a preformed dental tool or a dental tool is integral with the tool end of the shaft and extends away from the tool end.

2. A holder according to claim 1 in which the tool end of the shaft is adapted to receive a preformed dental tool within the shaft and the holder includes tool securing means for mounting the preformed dental tool at the tool end of the shaft.

3. A holder according to claim 2 in which the shaft portion is folded substantially parallel to the length of the holder to define a channel having a diameter less than the diameter of the tubular shaft and in which the tool can be fitted.

4. A holder according to claim 2 in which the shaft portion is folded to form a resiliently flexible clamp for receiving the tool and which can resist removal or movement of a tool held in the clamp.

5. A holder according to claim 2 in which the tubular shaft is adapted to be deformed to provide interlocking engagement with the tool.

6. A holder according to claim 2 further comprising the dental tool received within the shaft.

7. A holder according to claim 1 in which the first flange is narrower than the shaft portion and the drive surface which is formed by folding the flange is located radially inwards of the periphery of the shaft.

* * * * *